United States Patent
Gavaskar et al.

(10) Patent No.: US 7,396,470 B2
(45) Date of Patent: Jul. 8, 2008

(54) TREATMENT OF ENVIRONMENTAL POLLUTANTS WITH MINERAL ORES

(75) Inventors: Arun R. Gavaskar, Columbus, OH (US); Sandip Chattopadhyay, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 101 days.

(21) Appl. No.: 10/507,354

(22) PCT Filed: Mar. 12, 2003

(86) PCT No.: PCT/US03/07631

§ 371 (c)(1),
(2), (4) Date: May 31, 2005

(87) PCT Pub. No.: WO03/078030

PCT Pub. Date: Sep. 25, 2003

(65) Prior Publication Data

US 2006/0151395 A1     Jul. 13, 2006

Related U.S. Application Data

(60) Provisional application No. 60/396,526, filed on Jul. 17, 2002, provisional application No. 60/363,693, filed on Mar. 12, 2002.

(51) Int. Cl.
    *C02F 3/00*           (2006.01)
(52) U.S. Cl. .................. 210/688; 210/747; 210/764
(58) Field of Classification Search .............. 210/747, 210/764, 688
See application file for complete search history.

(56) References Cited

U.S. PATENT DOCUMENTS

| 2,391,116 | A | | 12/1945 | Ashley |
| 5,245,106 | A | * | 9/1993 | Cameron et al. ............ 585/823 |
| 2004/0031749 | A1 | * | 2/2004 | Koslow ..................... 210/505 |

FOREIGN PATENT DOCUMENTS

| DE | 19745191 | 4/1999 |
| DE | 19936930 | 2/2001 |

* cited by examiner

*Primary Examiner*—Chester T Barry
(74) *Attorney, Agent, or Firm*—Frost Brown Todd LLC

(57) ABSTRACT

A method for removing a pollutant from emissions or the environment comprising: contacting a mineral ore or the use of a mineral ore selected from the group consisting of bauxite, modified bauxite and mixtures thereof. Typically, the pollutant is a heavy metal or a microorganism.

6 Claims, 5 Drawing Sheets

TREATMENT OF ENVIRONMENTAL POLLUTANTS WITH MINERAL ORES

This application claims the benefits of U.S. Provisional Patent Application No. 60/363,693, filed Mar. 12, 2002; and U.S. Provisional Patent Application No. 60/396,526, filed Jul. 17, 2002. The entire text and drawings of the above mentioned provisional applications are hereby incorporated herein by reference as if completely rewritten herein.

FIELD OF THE INVENTION

The present invention discloses the use of several relatively raw materials including bauxite, iron ore (e.g. magnetite, hematite, goethite), feldspar, lignite and mixtures thereof for the amelioration of environmental pollutants and/or emissions. Typical pollutants in the emissions or the environment Include heavy metals such as arsenic, cadmium, chromium, nickel, mercury; microorganisms; organic solvents; and the like.

BACKGROUND OF THE INVENTION

Pollutants in or on the ground, or in surface or ground waters pose an increasing threat to the environment. The pollutants may result from industrial discharges, accidental spills, mine drainage, mine tailing seepage or leaks and the like. Typically, large quantities of polluted materials need to be treated so that cost of the treating materials becomes an important factor. The present invention seeks to answer this need by using low cost, readily available materials to bind the pollutants.

Heavy metals, such as mercury, arsenic, cadmium, chromium, and selenium, are used in a number of manufacturing operations and industrial and consumer products, but are hazardous to human health and the ecosystem when released to the environment. Often, heavy metals have to be removed from gas, water, or soil streams exiting a manufacturing facility or from the environment where they have already been released. The current invention proposes the use of bauxite or modified bauxite for removal of heavy metals from fluid streams (gases e.g. air or exhaust gas, liquids e.g. water), and soil or other aggregate material.

A number of different treatment processes and products have been proposed in the past for removal of these metals from the target matrices to prevent the metals from migrating to potential points of human exposure and to protect the environment. In gas streams (for example, consisting of coal-burning power plant emissions), metals are removed by using an adsorbent or catalyst. Activated carbon (Vidic R. D., Liu, W. (1997) Development of Novel Activated Carbon-Based Adsorbents for Control of Mercury Emissions From Coal-Fired Power Plants. DOE-NETL publication; Miller, S. J., Dunham, G. E., Olson, E. S., and Brown, T. D. (2000) Fuel Processing Technology 65/66:343-363; U.S. Pat. No. 6,402,813 B2) and noble metals, like molybdenum, cobalt, have been used in the past for their adsorptive and catalytic properties, respectively. A two-step process of oxidation of elemental mercury to a mercury compound, followed by its removal on an adsorbent (e.g., activated alumina) has previously been proposed (U.S. Pat. No. 5,607,496). More complex filters, for example those that involve a support material on which are synthetically deposited multiple components to address multiple pollutants, have also been proposed (U.S. Pat. No. 5,212,131).

Bauxite has sometimes been used in the past for treatment of pollutants in gases, often after expensive processing to a substance called activated bauxite. Activated bauxite is commonly generated by heating the bauxite to a temperature in the range from 400 to 1,000° C., in order to increase its surface area and improve adsorption. For example, U.S. Pat. Nos. 5,595,954 and 4,639,259 describe how activated bauxite or activated alumina (a purified form of bauxite) can be promoted by adding an alkali metal oxide to remove HCl from fluid streams. U.S. Pat. No. 4,973,459 describes the use emathlite and bauxite as sorbents for removing alkali from hot gases at temperatures up to 1,800° F., by using the sorbents in conjunction with coarse particulate materials and filter units in a moving bed. U.S. Pat. No. 4,865,629 describes a process for flitering fine particulates from a stream of hot gas by blending a fraction of particles removed by the cyclones back to the gas; this work mentions the use of diatomite or bauxite particles that can be blended into the gas stream to remove corrosive sodium and potassium vapors. U.S. Pat. No. 3,917,733 describes a two-step process for removing halogen-containing chemicals from a liquid hydrocarbon stream by using alumina or bauxite as adsorbents, and then using the spent liquid-stream adsorbents as adsorbents for treating gas streams. In all these applications, bauxite in an activated form (following heat treatment to 400° C. or above) is used primarily as an adsorbent, rather than in a raw or gently modified form as a catalyst to cause transformations of the target gas stream.

Many of these previous processes suffer from one or more of the following limitations:

1. The use of the reagent generates a waste product that interferes with its eventual reuse or disposal.
2. The reagent is too specific towards one or other target pollutant
3. A two-step process is required to obtain adequate removal of the pollutant metals. This increases the complexity of the process and cost of the treatment.
4. The reagent is relatively expensive and economic use of the reagent requires another process to regenerate and reuse the reagent.

The present invention addresses these limitations. The invention consists of a reagent that is commonly available, removes multiple pollutants, is relatively cheap and can therefore be disposed of after a single use.

BRIEF DESCRIPTION OF THE INVENTION

A process for treating gas, water, or soil containing heavy metals to prevent their migration in the environment is disclosed. The process involves contacting the heavy metals with a multi-functional sequestration agent, namely, bauxite or modified bauxite. Bauxite is used in its relatively natural form (except for appropriate size reduction to fit a particular application) or in modified form (for increased efficiency). Modifications to the raw bauxite include, but are not limited to, simple processes, such as wetting with water, mild heating to temperatures below 300° C., and/or soaking in solutions of common acids, bases, or salts. In the current invention, when bauxite is applied for treatment of gases, sulfur is an essential ingredient in the co-precipitation of pollutant metals as sulfides. The sulfur may already be present in the gas stream being treated (as in coal combustion gases) or it may be introduced into the treatment with the bauxite. When bauxite is applied to water or soil environments, sulfur is not an essential ingredient for removal of metal pollutants. An important feature of the current invention for treatment of air, water, or soil matrices, is that bauxite, being a relatively cheap material, is used as a single use reagent. No regeneration or reuse of the bauxite is required and the economics of the process promotes its single use and disposal.

The relatively unrefined raw minerals bauxite, iron ore (e.g. magnetite, hematite, goethite), feldspar, and lignite are used for in-situ treatment of is pollutants to clean up surface and subsurface environments, such as groundwater, soil, fractured rock, surface water, and sediments. These minerals, in their naturally occurring form, are environmentally benign, commonly available, and relatively inexpensive.

Other embodiments of the invention provide for the treatment emissions containing microorganisms or for the in-situ treatment of pollutants in or on the ground that contain microorganisms. Typically the microorganisms of interest are pathogenic. Treatment typically consists of contacting the emissions or contaminated site with the mineral ores described herein.

BRIEF DESCRIPTION OF THE DRAWINGS

In FIG. 1, ESP refers to an electrostatic precipitator.

DETAILED DESCRIPTION OF THE INVENTION AND BEST MODE

Figure 1:
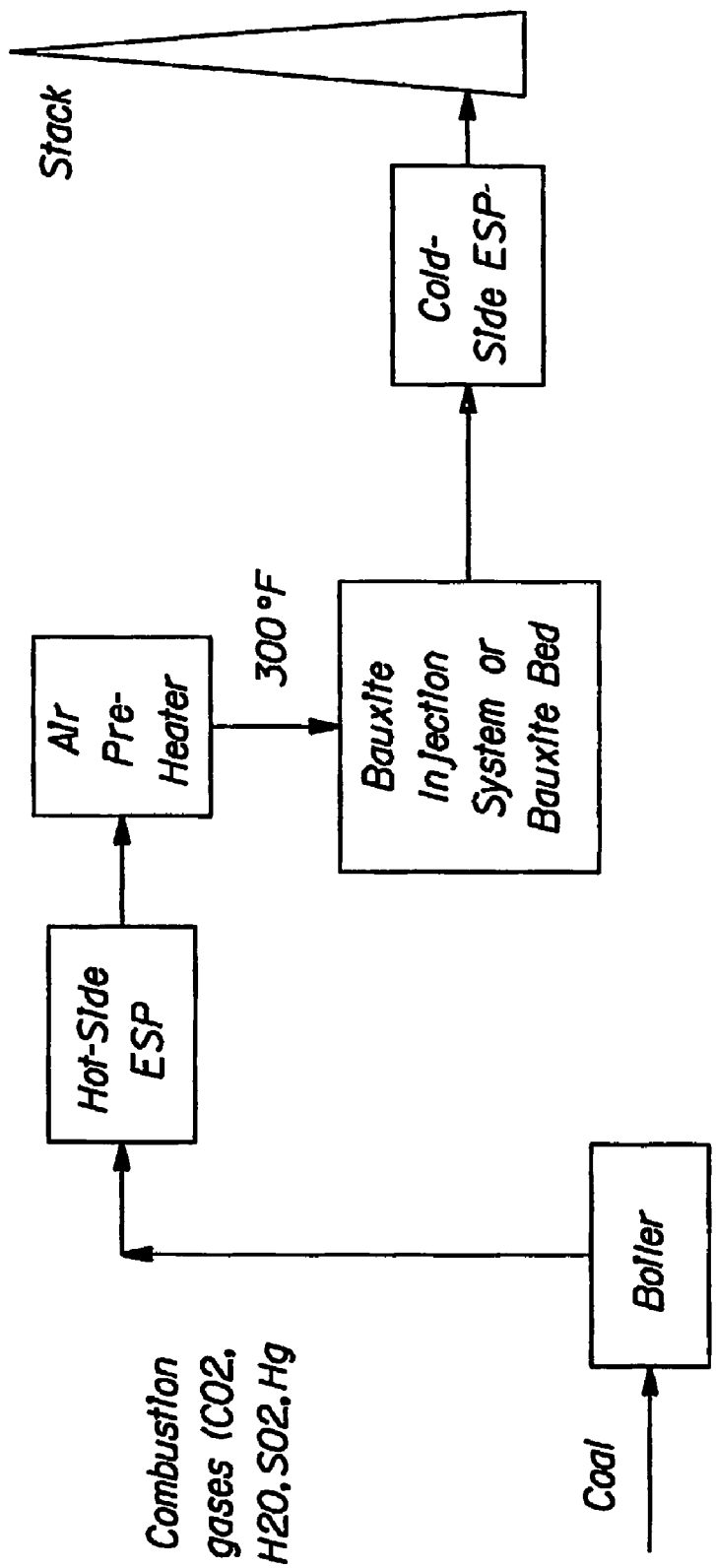
FIG. 1 is a schematic diagram depicting the use of bauxite to remove pollutant metals from combustion gas.

Broadly the invention include a process for treatment of heavy metals using a multi-functional sequestration agent.

One embodiment of the Invention consists of the use of bauxite, a common aluminum ore material, for sequestration of pollutant metals from gaseous phase (like flue gas), aqueous phase (surface water or groundwater), and solid phase (like soil or subsurface materials). The bauxite is used as its natural form or in a modified form that still retains the essential character of the bauxite. Modifications may include, but are not limited to, simple processes, such as wetting with water, mild heating to temperatures below 300° C., and/or soaking in solutions of common acids, bases, or salts. The modifications in the current invention aim to primarily increase the reactivity or catalytic properties of the bauxite, not necessarily its surface area (surface area enhancement is generally the goal of common heat treatments at 400° C. or higher that result in the manufacture of products called activated bauxite or activated alumina). For example, wetting with water enhances the reactivity of the bauxite (without increasing its surface area) by depositing hydroxyl ions on the bauxite surface.

In the case of gaseous streams, an additional essential ingredient in the current invention is the presence of sulfur. The sulfur may already be present in the target gas stream or may be introduced into the sequestration process, either through the gas stream or through addition to the bauxite. The sequestration of pollutant metals onto the reagent (bauxite) occurs through a combination of sulfide co-precipitation and adsorption.

In the case of pollutant metals in a water environments, bauxite works through a combination of co-precipitation and adsorption of the metals that come into contact with it. Even in soil or sediment (freshwater or marine) environments, the sequestration of pollutant metals occurs through migration of water through the soil or sediment, as the water enables the contact between the metals and the bauxite.

Broadly the invention also discloses use of the mineral ores such as bauxite (an aluminum ore), magnetite (an iron ore), hematite (an iron ore), goethite (an iron ore), feldspar (a Na—Al-silicate), or lignite, and mixtures thereof for the in situ treatment of pollutants to clean up surface and subsurface environments, such as groundwater, soil, fractured rock, surface water, and sediments. The pollutants may be dissolved or carried by surface or subsurface water. These minerals, in their naturally occurring form, are environmentally benign, commonly available, and relatively cheap.

The challenge with in situ (within or adjacent to the affected environmental medium) treatment of pollutants is to find treatment agents that are relatively inexpensive (that can be spread over a potentially large affected region), commonly available, and are compatible with the environment. The idea of using raw minerals in their naturally occurring form (without much prior processing) takes advantage of the fact that these minerals came from the environment and will be going back to the environment; this would create less of a regulatory concern. The three minerals bauxite, magnetite, and hematite were tested because they contain natural oxides or iron, aluminum, manganese, titanium and other oxide compounds, that can potentially react with transported pollutants, (e.g. heavy metals such as arsenic and mercury, and organic compounds), and prevent them from migrating towards potential receptors (such as drinking water wells, aquatic ecosystems, etc.). These three minerals are easily available in the United States and other countries in bulk; they are either mined in the country or, as in the case of bauxite, mined outside the country but consumed in large enough quantities, that they are available at reasonable cost. Other minerals useful with the invention include goethite, feldspar, and lignite. Typically, feldspar and lignite are contemplated for removal of mercury. Minerals, such as these, contain a variety of constituents that can react with pollutants and either adsorb or destroy them.

EXAMPLE 1

The first pollutant that was tested was arsenic. There is a great deal of interest in arsenic, especially because a reduction in the regulatory limit for this pollutant in drinking water has recently been made. The limit (health standard in the U.S.) for arsenic in drinking water has been reduced from 50 μg/L to 10 μg/L.

The Table 1 shows the results of several batch tests. Batch tests were conducted in small bottles containing a locally obtained groundwater. Arsenic was spiked into the water to levels of approximately 1,400 μg/L. The results show that arsenic levels in the water were reduced from approximately 1,400 μg/L to between about 19.8 μg/L and 86.4 μg/L when the mineral was added to the water and shaken on a shaker table for 24 hours. Nitrogen was bubbled through the water before the tests in order to remove dissolved oxygen and maintain the arsenic as As (III), versus As (V). The lower-valent arsenic is more difficult to treat and was considered a greater challenge for the test. The bottles were filled to the top with little or no headspace. After shaking, the bottles were centrifuged to settle out the mineral. The supernatant was then analyzed. The results are in the Table 1 below.

TABLE 1

Treatment with raw minerals for groundwater containing arsenic

| Test Sample | Arsenic Concentration (μg/L) | Removal |
|---|---|---|
| Initial Arsenic Concentration 1* | 1,350 | — |
| Initial Arsenic Concentration 2* | 1,420 | — |
| Magnetite, Repetition 1 | 76.9 | 94% |
| Magnetite, Repetition 2 | 86.4 | 94% |
| Hematite, Repetition 1 | 36.4 | 97% |
| Hematite, Repetition 2 | 20.9 | 99% |
| Bauxite, Repetition 1 | 20.0 | 99% |
| Bauxite, Repetition 2 | 19.8 | 99% |

*Pre-treatment concentration in the groundwater was approximately 1,400 μg/L of arsenic (as arsenite). Control runs were bottles without the mineral (just groundwater and arsenic).

Table 1 indicates that bauxite was the most efficient at removing arsenic, followed by hematite and magnetite. All three minerals achieved greater than 90% removal of arsenic (all % used herein are in weight percent). Natural minerals are a complex mix of chemical compounds. Not wishing to be bound by theory, it is presently thought that the compounds that have played a role in the adsorption and removal of arsenic from the groundwater were the mix of oxides of iron, aluminum, manganese, and titanium. However, other mineral constituents may have played a role in the removal as well.

EXAMPLE 2

Table 2 shows a second series of tests that were conducted to further test the performance of the minerals. Specifically, the two objectives of the second series were to: (a) determine whether the minerals can remove arsenic to the low levels required by the imminent new regulatory standard of 10 μg/L, and (b) to determine whether the arsenic would stay sequestered by the mineral or would re-dissolve over time. The target initial amounts of arsenic (as As [III]) that were spiked into groundwater were 100 μg/L, 50 μg/L, and 25 μg/L. The corresponding control bottles (no mineral phase added) showed 85.7 μg/L, 40.8 μg/L, and 20.1 μg/L respectively, after one day of mixing. After one day of mixing, the bauxite appeared to be the most efficient in arsenic removal, removing the arsenic present in the groundwater in all six bottles to less than 10 μg/L of arsenic, which is both the imminent regulatory standard and the present analytical detection limit.

TABLE 2

Treatment of varying initial dissolved concentrations of arsenic with minerals

| Mineral | Initial Concentration (μg/L) | Day 1 (μg/L) | Day 2 (μg/L) | Removal (%) |
|---|---|---|---|---|
| Bauxite | 85.7 | <10 | <10 | >88.3% |
|  |  | <10 | <10 | >88.3% |
|  | 40.8 | <10 | <10 | >75.5% |
|  |  | <10 | <10 | >75.5% |
|  | 20.1 | <10 | <10 | >50.2% |
|  |  | <10 | <10 | >50.2% |
| Magnetite | 85.7 | 27.3 | 12.2 | 68.1% to 85.8% |
|  |  | 26.0 | 12.4 | 69.7% to 85.5% |
|  | 40.8 | 13.2 | <10 | 67.6% to >75.5% |
|  |  | <10 | <10 | >75.5% |
|  | 20.1 | <10 | <10 | >50.2% |
|  |  | <10 | <10 | >50.2% |
| Hematite | 85.7 | 38.4 | 36.4 | 55.2% to 57.5% |

When the bauxite test bottles were shaken (mixed) for one more day, there were no signs that any of the sequestered arsenic was desorbed or otherwise released from the solid mineral. The same was true for magnetite and hematite, after two days of shaking.

Hematite and magnetite were not as efficient as bauxite under all conditions, but still removed between 55% to over 99% of the arsenic under some conditions. All three minerals reduced arsenic to below 50 μg/L, the current regulatory limit.

Raw bauxite ore typically contains varying proportions of aluminum oxide (35% to 65% as gibbsite, boehmite, and/or diaspore), silica (0.5% to 10% as quartz and/or kaolinite) and iron oxide (2% to 30% as goethite, hematite, and/or siderite), titanium oxide (0.5% to 8% as anastasite and/or rutile), and calcium oxide (0 to 5% as calcite, dolomite, and/or magnetite). Again not wishing to be bound by theory, it is presently believed that in addition to the aluminum oxide hydrates (the primary component of the bauxite ore), that the other constituents probably play an important role in the sequestration of pollutants, either through adsorption or chemical bonding or through sequestration in the varying mineralogical structure of the constituents.

EXAMPLE 3

The tests of Examples 1 and 2 are repeated for bauxite, magnetite, goethite, and hematite, except that mercury is used as the pollutant at a concentration of 10 μg/L, 20 μg/L, and 40 μg/L. Mercury is removed in these tests.

Microorganisms

Bauxite and allied mineral ores (e.g., copper, manganese, or titanium ores) are expected to be effective in adsorbing and inactivating pathogenic microorganisms that may be encountered in soil, water, or air environment. Therefore, these ores can be used for applications, such as (for example):
1. Protection of drinking water supplies through:
   (a) installation of a subsurface mineral ore barrier in the path of a migrating pathogen plume; or
   (b) running the extracted water at a drinking water plant through a cartridge consisting of the mineral ore.
2. Protection of indoor air from atmospheric releases of microbial pathogens by installing a mineral ore cartridge in the heating, ventilation, and air conditioning.
3. Controlling the spread of the microbes in soil by mixing granular or powdered ore with soil.

Most pathogenic microorganisms (e.g. bacteria and viruses) are negatively charged under natural environmental conditions. The state of charge of the microorganism (e.g. a virus) is expressed by a quantity known as the isoelectric point. This point is the value of pH at which the virus has a net charge of zero. The isoelectric points of Hepatitis A, Polio, Reovirus 3, and Coxsackie A21 are 2.8, 3.8, 3.9, and 4.8, respectively. Under normal environmental conditions, bauxite and other minerals (like Al, Cd, Mn ores and minerals) generally carry a positive charge. The point of zero charge of bauxite generally occurs between a pH of 7.53 and 8.29, depending on the electrolyte concentration. The point of zero charge of other mineral oxides are: $\alpha$-$Al_2O_3$, $\gamma$-AlOOH, CuO, $\alpha$-$Fe_2O_3$, are 9.1, 8.2, 9.4, and 8.6, respectively. These oxides, hydroxides, and other mixture of minerals are known for their oxidizing properties. Viral inactivation covers a wide range of phenomena, from mild, reversible inactivation (e.g., by nonspecific sorption on quartz sand) to severe, irreversible fragmentation of viral proteins by lysis (e.g., exposure to strong oxidants, chemisorption, etc.). Coordination of carbonyl groups from peptide linkages of sorbed viruses at the mineral surfaces may provide a conduit of electron transfer. Viral die-off may occur in the presence of active chemical sites on these barrier materials by a variety of mechanisms, including:

(i) disruption of the virus membrane;
(ii) blockage of the receptor-ligand interactions essential for infectivity;
(iii) inhibition of the replication of pathogens; or
(iv) alteration of the environment and reduction of the susceptibility of infection.

Typically, in practice the emissions of power plants, industry, medical facilities, homes, or other point sources are contacted with the mineral ores described herein so that the pollutants in the emissions are adsorbed, absorbed, chemically reacted, or otherwise inactivated.

In one embodiment of the invention, a gas stream containing pollutant metals passes through a bed of granular bauxite (see FIG. 1). An essential ingredient of the current invention for the application to gas streams is the presence of sulfur. The geochemical complexation in these solid-phase surfaces generates sufficient sulfide/bisulfide to precipitate contaminants metals as insoluble sulfides for long-term remediation of impacted sites. The thermodynamic parameters of the metal sulfides are given in Table 3. The low value of solubility product of metal sulfides indicates that these sulfides are very insoluble compound. Also, considering the Gibbs free energy ($\Delta G$) values of these metal sulfides, the net change in free energy reactions indicate that the reactions are thermodynamically favorable.

TABLE 3

Thermodynamic parameters of metal sulfide precipitates

| Metal sulfide | Gibbs energy of formation* ($\Delta Gf$) Kcal/mol | Equilibrium constant of formation* (log Kf) | Solubility product of metal sulfide (Ksp) |
|---|---|---|---|
| Arsenic(III) sulfide (As2S3) | −40.269 | 24.466 | |
| Chromium sulfide (CrS) | −32.893 | 24.111 | |
| Cadmium sulfide (CdS) | −34.868 | 25.559 | 8 × 10-7 |
| Copper(II) sulfide (CuS) | −13.440 | 9.851 | 6 × 10-16 |
| Mercury(II) sulfide (HgS) | −11.187 | 8.200 | 4 × 10-33 |
| Nickel(II) sulfide (NiS) | −21.462 | 15.732 | |
| Lead(II) sulfide (PbS) | −23.097 | 16.930 | 3 × 10-7 |

*Temperature at 298.15 K.

Figure 2:
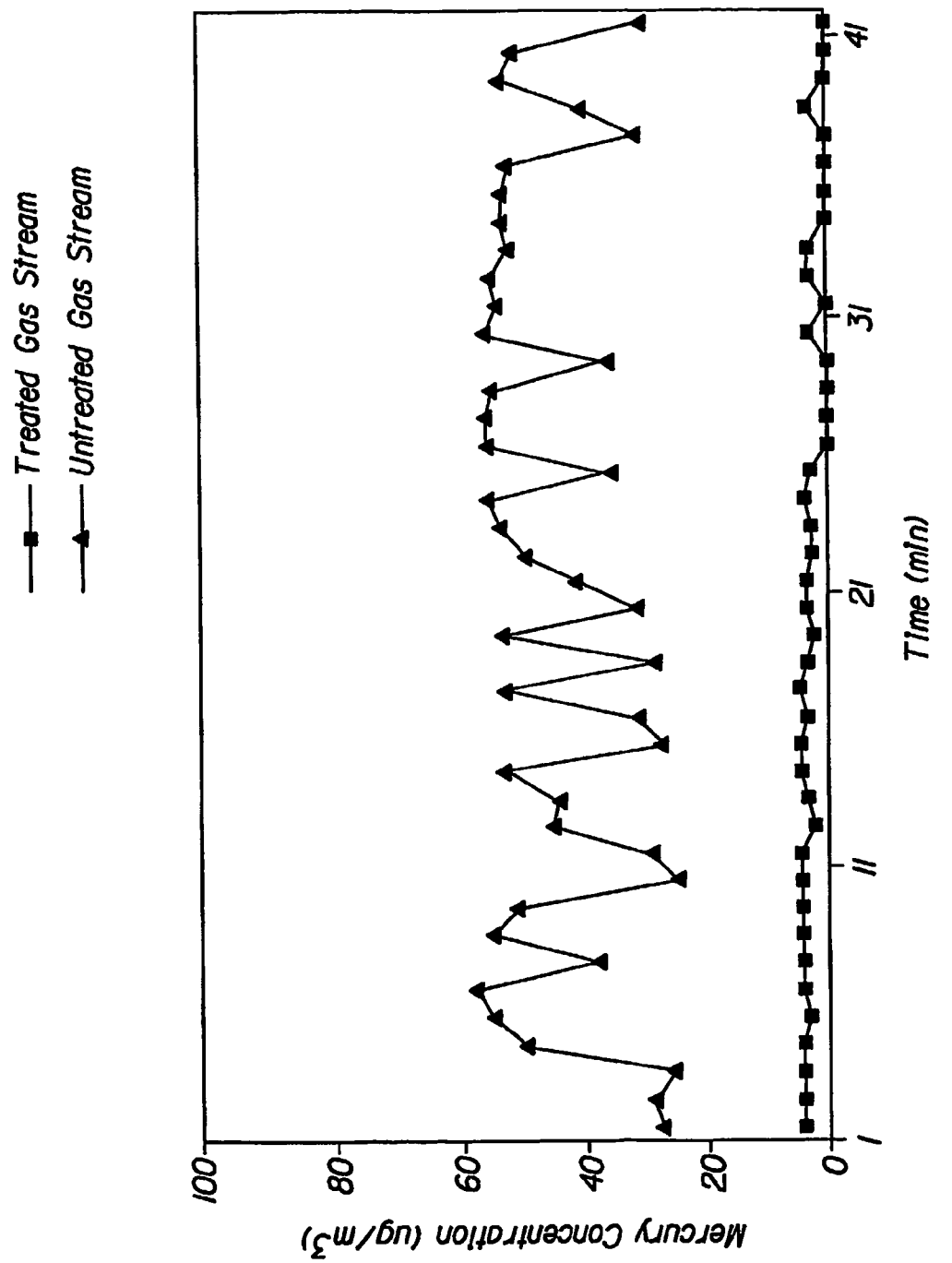
FIG. 2 is a graph that shows the results of a test run for removal of mercury form a gas stream using bauxite.

The sequestration happens through one or more of the following processes: surface oxidation, hydrolysis, surface catalyzed precipitation, and/or incorporation by recrystallization and coprecipitation. The bauxite is multi-functional in this environment because it causes the removal of both positively charged (e.g., mercury and/or selenium) and negatively charged (e.g., oxyanions of arsenic or chromium) of metals. Surface complexation reactions are responsible for removal of both cationic and anionic species. A previous patent (U.S. Pat. No. 20010000475) has proposed the use of various catalysts for reducing SO2 to elemental sulfur, but the production of sulfides is mentioned as an "undesirable byproduct". The current patent makes use of this sulfide production to coprecipitate out the pollutant metals. Unlike activated carbon, sequestration with bauxite is effective over a wide range of temperatures ranging from below ambient to the high temperatures encountered in combustion gases and incinerator exhausts. FIG. 2 shows the results of influent and effluent mercury measurements in a simulated coal combustion gas stream flowing over a bed of bauxite. Bauxite in its natural form, crushed to −8+50 mesh size range was used in this test. The presence of SO2 in the gas stream facilitates the coprecipitation of mercury as a sulfide.

In a second embodiment of the invention the bauxite is introduced in a powdered form into the gas stream. In the powdered form, the bauxite is much more reactive with the SO2 and metals. Also, injection of bauxite powder can be implemented without increasing the pressure drop (and energy requirement) in the flue gas equipment in a power plant. The mercury would be recovered along with the fly ash. In a fixed bed of bauxite, additional pressure drop would be introduced into the flue gas system, but the mercury can be recovered separate from the fly ash. In either case, the mercury is in a much less bio-available form.

In a third embodiment, the bauxite is modified to enhance its sequestration capability while retaining its essential character. One modification that enhances sequestration is wetting of the bauxite surfaces with water. Other modifications include, but are not limited to, hydroxyl, sulfonyl, thiol moieties associated with the surface. These functional groups improve the metal removal efficiency. The modifications will be limited to simple processes, such as soaking the bauxite in solutions of acids, bases, or salts. Any heat treatment will involve milder temperatures (300° C.) or less compared to the temperatures typically involved in manufacture of activated bauxite (400° C. or more).

Figure 3A:
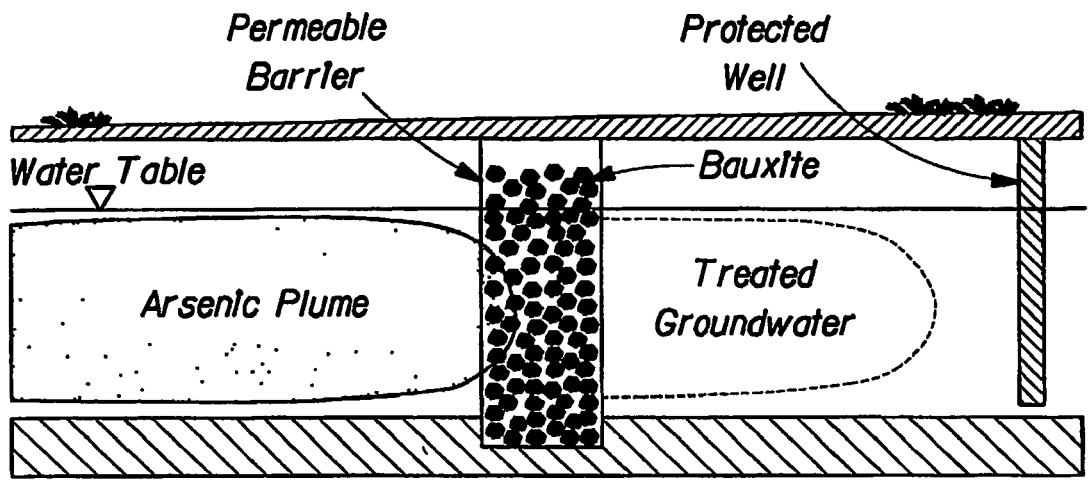
FIGS. 3(a) and 3(b) are schematic diagrams depicting the treatment of ground water pollutants using a permeable barrier consisting of bauxite The bauxite can be either be placed as granular material in a trench, or injected as a powder into deeper aquifers.
Figure 3B:
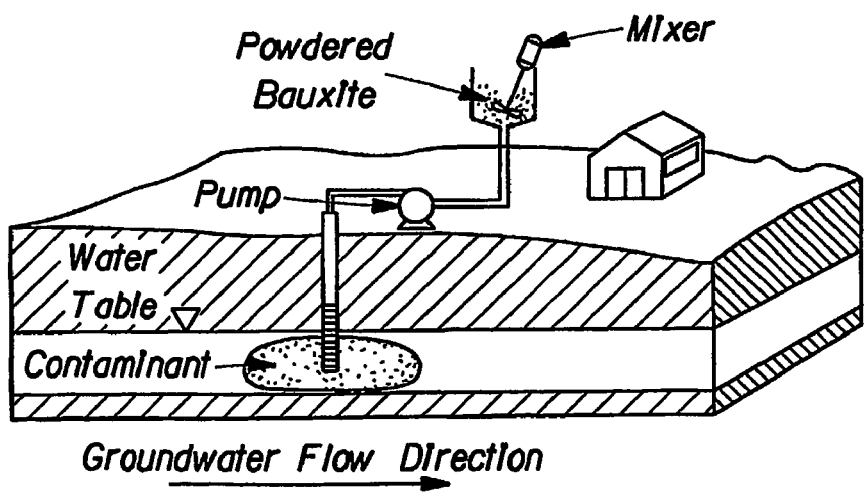

In a fourth embodiment, the bauxite is applied in granular form as a permeable medium for the in situ treatment of groundwater (see FIGS. 3a and b). Sulfur is not an essential ingredient in the sequestration of pollutant metals in water or soil environments. Table 4 shows the results of experiments conducted with groundwater containing mercury, arsenic, cadmium, and chromium. All these metals were substantially removed by the bauxite.

TABLE 4

Treatment of metals in groundwater with bauxite

| Barrier Material | Target Contaminant | Initial Concentration (ug/L)* | Final Concentration (ug/L) after 1 day** | Removal |
|---|---|---|---|---|
| Bauxite −8+50 mesh | Arsenic | 25 | <10 | >60% |
| | Arsenic | 50 | <10 | >80% |
| | Arsenic | 100 | <10 | >90% |
| | Arsenic | 200 | <10 | >79% |
| | Arsenic | 2,000 | 198 | 91% |
| Bauxite −8+50 mesh | Mercury | 20 | <0.5 | >98% |
| | Cadmium | 1,000 | 121 | >87% |
| | Chromium | 1,000 | <10 | >99% |
| Bauxite <200 mesh | Arsenic | 2,000 | <10 | >99% |

Bauxite was among several adsorbents previously examined for possible use in water treatment (Saha, I., K. Dikshit, and M. Bandyopadhyay. Comparative Studies for Selection of Technologies for Arsenic Removal from Drinking Water. Proceedings of BUET-UNU International Workshop on Technologies for Arsenic Removal from Drinking Water. Dhaka, Bangladesh, May 5-7, 2001), but it was eliminated after the first screening and subsequent rounds of testing focused on materials that provided the much higher arsenic efficiency that would be required in a water treatment unit installed in individual homes or drinking water plants for point-of-use treatment. This disenchantment with bauxite for home use is understandable because a very high efficiency, high capacity adsorbent is required that can remove arsenic from water within a few seconds or less of contact time available in home use systems. Others (U.S. Pat. No. 6,030,537) have tried to create special adsorptive materials with high adsorption efficiency, for example, by using a material called activated bauxite, in which bauxite is modified by heat treatment at 350 to 700° C. Activated bauxite was tested by Itself and in combination with aluminum tri-hydrate by the said others. However, heat treatment is energy intensive and expensive and is unnecessary for the current invention. In this embodiment of the current invention, where bauxite is applied as a permeable medium for in situ treatment of groundwater, high efficiency and high capacity are not as important as easy availability and low cost. This is because groundwater flows very slowly (typically 1 foot per day or less linear velocity). In this situation, the contact time available to the water as it flows through the bauxite medium is of the order of several hours or days. Because the bauxite material is cheap, it can be installed as a treatment medium that is several feet thick in the path of the groundwater flow to provide the longer contact times and to provide moderately high sequestration capacity. Bauxite can therefore be effectively applied in situations where slightly longer contact times can be arranged. Alternatively, in the current invention the reactivity of the bauxite may be modified or improved without heat treatment, for example, by soaking the bauxite in or wetting it with a solution of common acids, bases, or salts. This is a simpler and much less expensive modification than heat treatment.

Figure 4A:
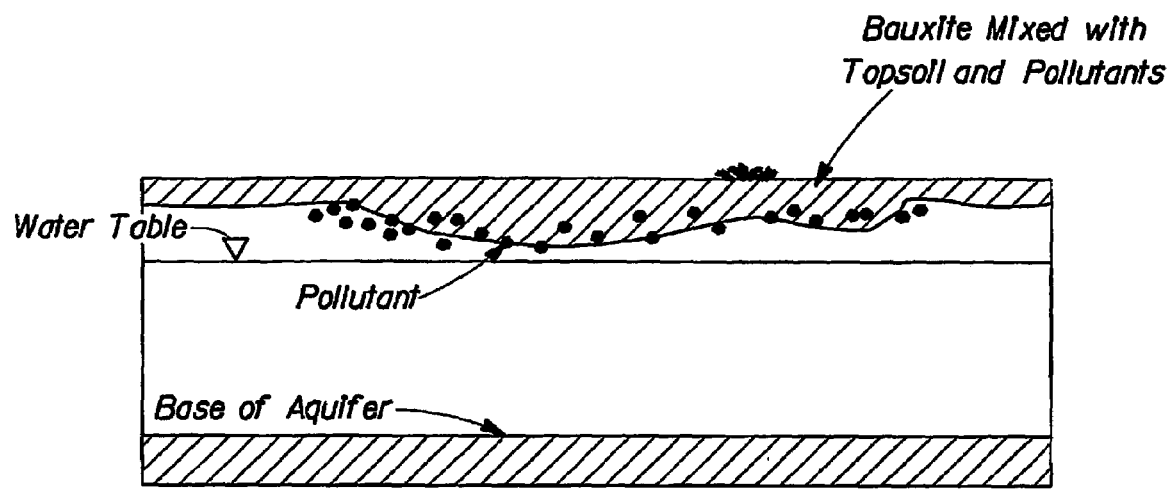
FIG. 4(a) shows the mixing of bauxite with surface soils to sequester pollutants.
Figure 4B:
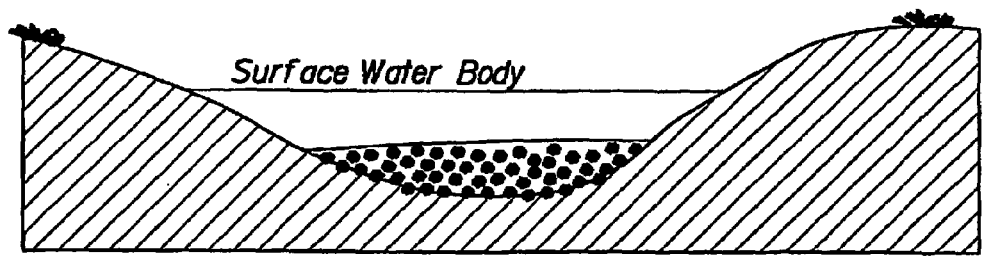
FIG. 4(b) shows the placement of bauxite on top of contaminated sediments to prevent migration of pollutants to the water body above.
Figure 5:
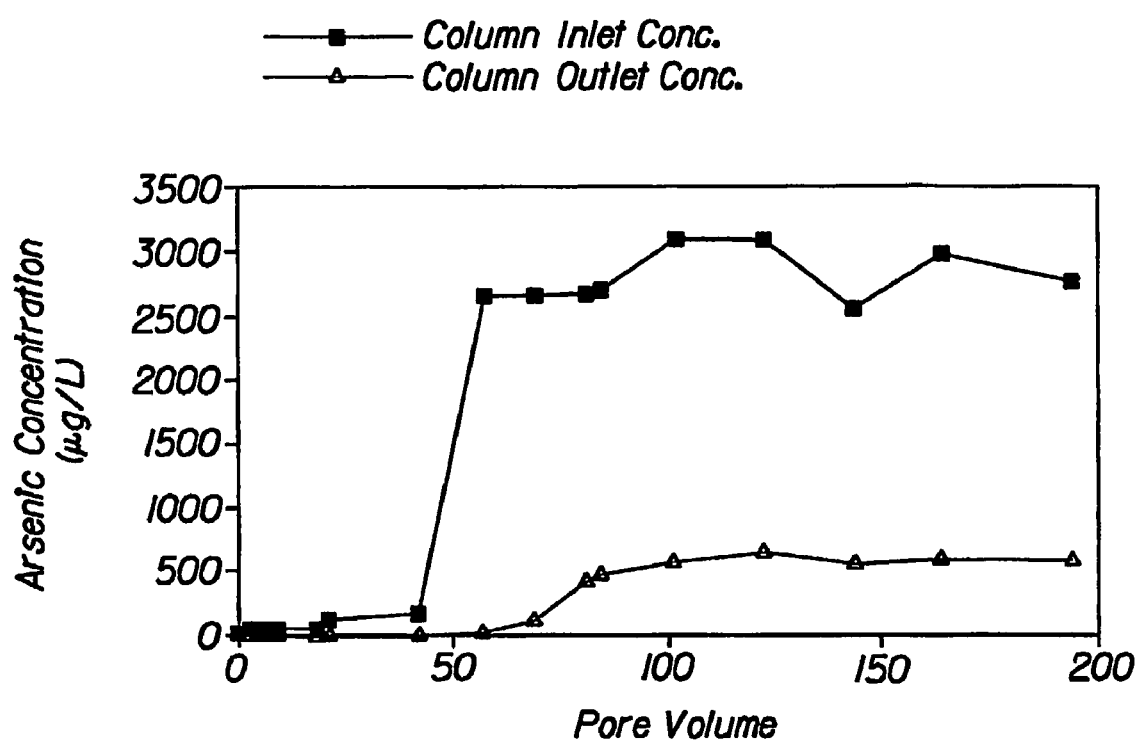
FIG. 5 shows that the pollutant removal of bauxite can be sustained long enough for the treatment to be economical.

In a fifth embodiment, the bauxite is applied as a cap over contaminated sediments under surface water bodies to prevent the migration of metal pollutants from the sediments to the water column above (see FIGS. 4a and b). Table 5 shows the results of experiments conducted with sediments from two sources, New York Harbor and Sequim. In each case, bauxite removed the pollutant metals substantially.

In a sixth embodiment, the bauxite is applied as a treatment for scrubber water exiting a power plant. In power plants that have scrubber, many of the heavy metals in the combustion gases are removed in the scrubber water and the water has to be treated before discharge. This water could be passed through a bed of granular bauxite. Alternatively, powdered bauxite could be added to the water and then separated out by settling or filtration.

In all these embodiments, bauxite, a relatively cheap sequestering agent is not regenerated and is applied as a single use reagent. This enhances the economic attractiveness of the treatment process. For example, during treatment of combustion gas streams, powdered bauxite is injected into the gas and the metals-laden bauxite is collected downstream with the fly ash. The bauxite and the sequestered metals are disposed or reused according to the ongoing convention at the plant. The metals being in a non-mobile, non-bio-available, sulfide form on the bauxite their subsequent potential leachability to the environment is very limited. The waste product (e.g., fly ash) can therefore be safely reused in a variety of products. In the case of treatment of groundwater or sediments, the bauxite can be permanently left in the environment after it has served its purpose.

While the forms of the invention herein disclosed constrate presently preferred embodiments, many others are possible. It is not intended herein to mention all of the possible equivalent forms or ramifications of the invention. It is to be understood that the terms used herein are merely descriptive, rather than limiting, and that various changes may be made without departing from the scope of the invention.

We claim:

1. A method for treating water, sediment or soil containing pollutants by the step of contacting pollutant-containing water, sediment, fractured rock or soil with a multi-functional sequestration agent comprising bauxite in it relatively natural form, wherein said bauxite is installed as a subsurface mineral ore barrier.

2. A method for treating water, sediment or soil containing pollutants by the step of contacting pollutant-containing water, sediment, fractured rock or soil with a multi-functional sequestration agent comprising bauxite in its relatively natural form, wherein said bauxite is in a permeable barrier, and wherein said permeable barrier is installed in the path of groundwater flow.

3. A method for treating water, sediment or soil containing pollutants by the step of contacting the pollutant-containing water, fractured rock or soil with a multi-functional sequestration agent comprising bauxite in its relatively natural form, wherein said water is groundwater.

TABLE 5

Sequestration of Mercury in Sediment by Bauxite

| Matrix | Initial Concentration of Hg in Sediment Supernatant (ug/L) | Final Concentration of Hg in Sediment Supernatant After 48 Hrs (ug/L) | Final Concentration of Hg in Sediment Supernatant After 96 Hrs (ug/L) | Removal Percentage of Hg by Bauxite After 48 Hrs (%) | Removal Percentage of Hg by Bauxite After 96 Hrs (%) |
|---|---|---|---|---|---|
| New York Harbor Sediment | 249.8 | 26.5 | <0.20 | 89.39 | >99.0 |
|  | 243.5 | 31.2 | <0.20 | 87.19 | >99.0 |
| Sequim Sediment | 256.5 | 57.5 | <0.20 | 77.58 | >99.0 |
|  | 251.4 | 53.4 | <0.20 | 78.76 | >99.0 |
| Hg Control | 241.2 | 237.8 | 238.1 | N/A | N/A |

4. A method for removing or inactivating microorganisms in an emission or in the environment comprising contacting the microorganisms with a mineral selected from bauxite, cooper ores, and mixtures thereof, wherein if the mineral is bauxite it is installed as a subsurface mineral ore barrier.

5. A method for removing or inactivating microorganisms in an emission or in the environment comprising contacting the microorganisms with a mineral selected from bauxite, copper ores, and mixtures thereof, wherein if bauxite is used it is in a permeable barrier, which is installed in the path of groundwater flow.

6. A method for removing or inactivating microorganisms in an emission or in the environment in groundwater comprising contacting the microorganisms with a mineral selected from bauxite, copper ores, and mixtures thereof.

*